United States Patent
Chahal et al.

(10) Patent No.: US 8,048,846 B2
(45) Date of Patent: Nov. 1, 2011

(54) PROTEIN-SILANE/SILOXANE COPOLYMERS, THEIR PREPARATION AND THEIR USE

(75) Inventors: Surinder Pall Chahal, Cheshire (GB); Alun Robert Barnes, Manchester (GB); Nicholas Ian Challoner, South Yorkshire (GB)

(73) Assignee: Croda International PLC, North Humberside (GB)

( * ) Notice: Subject to any disclaimer, the term of this patent is extended or adjusted under 35 U.S.C. 154(b) by 1776 days.

(21) Appl. No.: 10/388,180

(22) Filed: Mar. 14, 2003

(65) Prior Publication Data

US 2003/0235554 A1    Dec. 25, 2003

(30) Foreign Application Priority Data

Mar. 14, 2002 (GB) .................. 0206048.1

(51) Int. Cl.
- *A61K 38/00* (2006.01)
- *A61K 51/00* (2006.01)
- *C01B 33/04* (2006.01)
- *C09K 3/00* (2006.01)
- *B01D 19/04* (2006.01)

(52) U.S. Cl. ......... 514/1.1; 423/347; 516/117; 424/1.69
(58) Field of Classification Search .................. 514/2
See application file for complete search history.

(56) References Cited

U.S. PATENT DOCUMENTS

| 4,645,811 | A |   | 2/1987  | Falcetta et al. |
|-----------|---|---|---------|-----------------|
| 5,412,074 | A | * | 5/1995  | Jones et al. ............. 530/353 |
| 5,679,819 | A | * | 10/1997 | Jones et al. ............. 556/418 |
| 5,753,214 | A |   | 5/1998  | Yoshioka et al. |
| 6,228,968 | B1|   | 5/2001  | Yoshioka et al. |
| 6,358,501 | B1| * | 3/2002  | Dietz et al. ............. 424/70.12 |

FOREIGN PATENT DOCUMENTS

| EP | 0540357 |    | 5/1993 |
|----|---------|----|--------|
| EP | 0699431 |    | 3/1996 |
| EP | 0994144 |    | 4/2000 |
| EP | 0994144 | A2 * | 4/2000 |
| JP | 60241448 |   | 11/1985 |

OTHER PUBLICATIONS

Patent Abstracts of Japan; vol. 2002, No. 7, Jul. 3, 2002.
International Search Report dated May 19, 2003.
Patent Abstracts of Japan; vol. 2002, No. 7; Jul. 3, 2002.

* cited by examiner

*Primary Examiner* — Maury Audet
(74) *Attorney, Agent, or Firm* — Novak Druce + Quigg LLP

(57) ABSTRACT

The present invention provides a protein-silane and/or protein-siloxane copolymer obtainable by reacting a protein and a silane compound, the relative amounts of the protein and the silane compound being such that in the range of from 0.1 to 0.4 silane molecule is present for each reactive amino group of the protein. The copolymer is suitable for use in hair treatment compositions and is useful in reducing damage to hair caused by flexure and/or abrasion thereof.

16 Claims, 3 Drawing Sheets

PROTEIN-SILANE/SILOXANE COPOLYMERS, THEIR PREPARATION AND THEIR USE

The present invention relates to novel protein-silane and/or -siloxane copolymers, useful in the preparation of hair care compositions and, in particular, their use in shampoos, conditioners and other hair treatments for extending flex-abrasion lifetimes of hair fibers.

The need for hair conditioning products is well-known. Such products may address various problems encountered with hair, for example, by treatments such as bleaching or coloring or by environmental factors, such as sun, heat and pollution. Some conditioning products are also directed at improving qualities of the hair such as shine or combability. Various combinations of these advantages attributed to conditioning products may also be claimed for shampoos and styling agents, which may contain conditioning agents as well as the usual cleansing or styling agents.

U.S. Pat. No. 5,993,792 relates to customized multi-component hair composition in which compositions such as shine enhancers, moisturizers, herbal additives, hair strengtheners, vitamin additives, colorants, hair thickening agents and the like can be included. The strengthening compositions can contain a strengthening agent to penetrate the hair to help condition, strengthen and retain moisture in fine, limp hair and protein-deficient hair or to provide deep conditioning for dry or chemically processed hair. Such strengthening compositions typically include one or more plant or animal-derived proteins or amino acids or a combination thereof; exemplified is an aqueous mixture of plant-derived proteins comprising Vegequat W; Crodasone W; and Cropeptide W. However, no information is given about the specific effect of such proteins or mixtures thereof on hair.

European patent specification no EP 681 826 describes a water-based hair treatment preparation consisting essentially of hydrolysed wheat protein and wheat oligosaccharides, wheat amino acids and panthenol. Exemplified are tests on hair of the effect of the composition on tensile strength (stress-strain behavior) and moisture content. Tensile test methods make use of an apparatus in which a segment of the fiber, fixed at either end, is subjected to increases in extension during which the load is continuously monitored.

Several parameters might be derived from load-extension curves for treated hairs that, in comparison with those for untreated fibers, show the particular treatment has increased their tensile strength. Unfortunately, some of these parameters are not very realistic in relation to the physical conditions to which hairs are normally subjected on the head during cosmetic processing and manipulation ('dressing'). Thus, parameters such as 'load to break' or 'the post yield modulus' are often measured under conditions that, were they to have occurred on the head, would have extracted the hair from its follicle. Therefore, although tensile test methods have been successfully used to demonstrate improvements in the mechanical properties of hair, they access only one aspect of the physical processes of hair fracture that the consumer normally uses to evaluate the strength of hairs on the head. A more realistic test would involve all the elements—fiber bending (flexure), abrasion and extension—encountered in normal hair fracture.

A test, referred to hereinafter as the 'flexabrasion test', which measures an amalgamation of all three elements outlined above, has been developed in the prior art. The test is carried out using equipment specifically designed to assess the fatigue lifetime of a strand of hair through bending and straightening. This equipment has been built to mimic the interaction of hair against hair on the human head when it is being brushed. When a brush is pulled through the hair, the hair strands are entwined and move against one another, causing longitudinal shear within the fiber shaft, which will eventually cause longitudinal splitting and premature fracture. As illustrated in FIG. 1 of the present specification, damage to the hair shaft is mimicked with this equipment as each strand of hair is being moved backwards and forwards over a piece of drawn rough tungsten wire. The method is described and illustrated in more detail in the article 'Flexabrasion: A Method for Evaluating Hair Strength' by J. A. Swift, S. P. Chahal, D. L. Coulson and N. I. Challoner, Cosmetics and Toiletries, 2001, Cosmetics & Toiletries Magazine 2001, Vol 116, No 12, Pages 53-60, the entire contents of which are incorporated herein by reference thereto.

The applicant's European patent specification no EP 540 357 describes the preparation of a protein-silane and/or -siloxane copolymer wherein the silane and/or -siloxane component is covalently bonded to amino groups of the protein and at least some of the silane and/or -siloxane component forms cross-links between different protein chains, the protein component forming from 5% to 98% by weight of the polymer. The whole content of this specification is incorporated herein by reference. The copolymers disclosed in EP 540 357 exhibit excellent conditioning properties, such as enhanced substantivity to skin and hair, and excellent wet and dry combing behavior.

The copolymers exemplified in EP 540 357 are formed from proteins having weight average molecular weights ranging from 3500 Daltons (D) to 10000 D and are reacted with a stoichiometric amount of silane such that the degree of modification of the protein amino groups is between 48% and 82%. Typically, the reaction and the subsequent cross-linking of the protein-silane copolymer produces a copolymer of large weight average molecular weight (generally in the range of 100-150 kD).

In particular, the copolymer of Example 2 of EP 540 357, which is commercially available under the trade mark Crodasone W, is formed by reacting a hydrolysed wheat protein having a weight average molecular weight of approximately 10000 D with a stoichiometric amount of silane such that the degree of modification of the protein amino groups is 60%. Quaternization of the remaining amino groups by the attachment of lauryl dimethyl quat groups to the copolymer resulted in a copolymer having a degree of modification of 85%.

Such products form a film on the surface of human hair, thereby imparting excellent surface properties such as wet and dry combability to hair treated with shampoo systems incorporating the product. However, such compounds have no effect on the flexabrasion properties of hair.

There is therefore a need for a composition that can effect an improvement of the fatigue lifetime of hair, especially hair that has been subjected to adverse conditions or treatments, particularly bleaching, coloring and/or perming. Especially, there is the need for a composition that will address the particular requirements of bending and straightening of the hair, and also hair-hair interactions, especially friction or abrasion, during dressing, such as brushing, of the hair.

We have surprisingly found that protein-silane and/or protein-siloxane copolymer compositions wherein the proportion of reactive amino groups of the protein which are modified by reaction with the silane is lower than those compositions disclosed in the prior art impart a substantial improvement of the fatigue lifetime, and particularly the flex-abrasion properties, of hair treated with these compositions when compared with the compositions known in the prior art.

Accordingly, the present invention provides a protein-silane and/or protein-siloxane copolymer obtainable by reacting a protein and a silane compound, the relative amounts of the protein and the silane compound being such that in the range of from 0.1 to 0.4 silane molecule is present for each reactive amino group of the protein.

In further aspects, the present invention provides the use of a protein-silane and/or protein-siloxane copolymer composition in the preparation of a composition for reducing damage to hair caused by flexure and/or abrasion thereof.

The invention also provides the use of a protein-silane and/or protein-siloxane copolymer in the preparation of a composition for increasing the mean flexabrasion lifetime, as defined herein, of hair fibers.

In further aspects, the present invention provides the use of a protein-silane and/or protein-siloxane copolymer composition, as defined above, in the preparation of a composition for reducing damage to hair caused by flexure and/or abrasion thereof.

The invention also provides the use of a protein-silane and/or protein-siloxane copolymer, as defined above, in the preparation of a composition for increasing the mean flexabrasion lifetime, as defined herein, of hair fibers.

Use of the copolymer compositions according to the present invention not only improves tensile strength of the hair treated therewith, but also improves bending modulus and inter-fiber friction, thereby significantly reducing the damaging effects of chemical and environmental stress on the hair.

Figure 1:
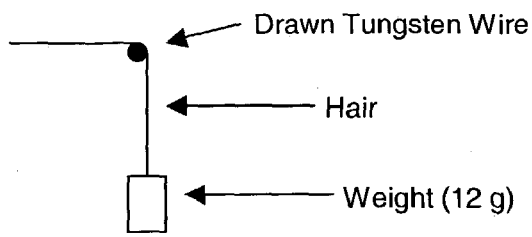
FIG. 1 is a schematic representation of a flexabrasion test apparatus for mimicking damage to hair from brushing comprising a piece of drawn rough tungsten wire upon which each strand of hair is moved backward and forwards.

In order to form the protein-silane and/or protein-siloxane copolymer of the present invention, the the protein and the silane compound are reacted such that in the range of from 0.1 to 0.4, especially about 0.2, silane molecule is present for each reactive amino group of the protein. When 0.2 silane molecule is present for each reactive amino group of the protein, the resulting copolymer comprises in the range of from 10 to 15% silylated amino groups and in the range of from 85 to 90% unreacted amino groups.

We have found that treatment of hair with the copolymer compositions according to the present invention imparts significant improvements to the flexabrasion lifetime, as described herein, of such hair when compared with hair treated with compositions described in the prior art. This is particularly the case for hair that has undergone adverse treatment such as bleaching, coloring, relaxing and/or perming (especially bleaching).

We have also found that treatment of hair with the copolymer compositions according to the present invention confers a significant reduction in damage to hair caused by flexure and/or abrasion thereof when compared with hair treated with compositions described in the prior art. This is particularly the case for hair that has undergone adverse treatment such as bleaching, coloring and/or perming (especially bleaching).

Preferred copolymers for use according to the invention are those wherein the copolymer is the reaction product of a protein hydrolysate and an organofunctional silane. More preferably, the organofunctional silane comprises an epoxysilane capable of reacting with one or more amino groups of the protein, such as glycidoxypropyltrimethoxysilane.

The protein may be derived from either animal or vegetable sources or by fermentation. It may be in the form of a chemically modified protein (for example, quaternized) provided that some free amino groups are still present in the protein molecules. Examples of proteins which are currently used in cosmetic formulations and which can be used as the protein component of the copolymer, include collagen, elastin, keratin, casein, wheat protein, soya protein and silk. In this specification, the term "protein" is used to include both native and hydrolysed proteins and it thus comprises both proteins properly so-called and polypeptides, peptides and peptones, since the latter can all be categorized as hydrolysed proteins.

The average molecular weight of the protein component may be from 200 Daltons (D) to 500 kD, is preferably within the range of from 295 D to 50 kD and is more preferably within the range of from 295 D-25.5 kD, even more preferably 350-1000 D, expressed as weight average molecular weight ($M_w$) derived from size exclusion chromatography. Protein-silane and/or protein-siloxane copolymers wherein the weight average molecular weight of the protein component is in the range of 600-800 D are particularly preferred, as treatment of hair with compositions containing such copolymers confers a particularly marked reduction in flexabrasion damage.

The copolymer suitably has a weight average molecular weight ($M_w$) in the range of from 295 D to 100 kD, such as in the range of from 2 to 64 kD, preferably in the range of 1.5 to 3 kD. In one particular example, the copolymer has a weight average molecular weight of 2611D.

Especially preferred is when the protein hydrolysate is a vegetable protein hydrolysate, particularly wherein the vegetable protein hydrolysate is of potato or wheat origin.

It is necessary for the protein component to be capable of solution in water or other suitable solvent or co-solvent (such as alcohol, eg propylene glycol or polyethylene glycol) to enable reaction to occur.

The organofunctional silane reactant is preferably soluble in a solvent common to the protein for efficient reaction. The conditions for reaction of the organofunctional silanes with the protein to achieve the desired degree of reaction and cross-linking must be carefully controlled, but will be apparent to or readily determinable by those skilled in the art of protein modification.

The organofunctional silane used for reaction with the protein component to form the copolymer must contain a functional group capable of reacting with the chain terminal and/or side chain amino groups of the protein. Suitable reactive groups include, for example, acyl halide, sulphonyl halide, anhydride, aldehyde and epoxide groups. The silicon component of the copolymer may be any compound which contains a siloxane group (Si—O—Si) or any silane capable of forming a siloxane in situ by condensation of silanol (Si—OH) groups (see Reaction 1 below) or any alkoxysilane or halosilane which hydrolyses to form a corresponding silanol (see Reaction 2 below) and then condenses to form a siloxane group (Reaction 1).

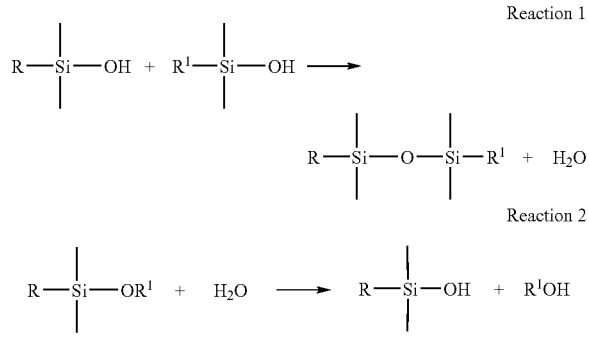

The silicone reactant is preferably capable of forming cross-links with the protein component. Cross-linking may be effected either through the use of polyfunctional silicone reactants or of monofunctional silicone reactants containing silanol groups (or alkoxysilane or halosilane groups convertible to silanol groups by hydrolysis) capable of forming siloxane cross-links by condensation between different chains. Such monofunctional silicone reactants should therefore have at least one and up to three hydroxy groups attached to at least one silicon atom in their structure. Generally, but not necessarily, the silanol group(s) will be in part of the reactant molecule remote from the amino-reactive organofunctional group.

For reaction of the protein amino groups to occur, it is usually necessary for the pH of the system to be above pH 7 and preferably within the pH range of 8 to 11.5. The reaction may be carried out at room temperature, but an elevated temperature and more preferably a temperature of from 30-80° C. is preferably used.

A suitable method for the manufacture of copolymer compositions for use according to the invention is represented by the following steps:

In a suitable vessel, the protein component is heated and the pH adjusted to alkaline to deprotonate the amino groups. A calculated quantity of silane (this is based on the Formol titer, a technique described by Cobbett, W. G., Gibbs, J. A. and Leach, A. A. (1964). *J. Appl. Chem.* (London), 14, 296-302.) to estimate the degree of modification of amino groups in proteins) is then added—the amount of silane is calculated to modify 5-40%, preferably 10-40% of the available amino groups. Following reaction, the pH is adjusted to acidic, and worked up in a conventional manner. Conventional additives, such as preservatives, may then be added.

A preferred method for the manufacture of copolymer compositions for use according to the invention is represented by the following steps:

1. Load the protein component, preferably hydrolysed vegetable protein, into a suitable tank and heat to 30-60° C. (preferably 40-50° C.).
2. Adjust pH to 9.5-11.0 (preferably 10.0-10.5) with sodium hydroxide.
3. Add calculated quantity of silane (this is based on the Formol titer, referred to above) and is calculated to modify 5-40% (preferably 10-20% of the available amino groups) over a 60-240 minute period (preferably 90-120 minute period).
4. Maintain temperature at 30-60° C., preferably 40-50° C., and pH at 9.5-11.0, preferably 10.0-10.5, during silane addition.
5. Maintain reaction conditions for a further 3-7 hours (preferably 4-5 hours).
6. Acidify to pH 3.5-5.5 (preferably 4.0-5.0) with a mineral acid, such as hydrochloric acid.
7. Preserve by addition of a preservative.
8. Cool and adjust pH to pH 3.5-5.5 (preferably 4.0-5.0).
9. Filter through a depth filter pad to sparkling.

Therefore, the copolymer composition produced also comprises (unreacted) protein hydrolysate. The copolymer composition may comprise silanol-terminated copolymer and/or siloxane cross-linked copolymer. The amount of silanol-terminated copolymer and/or siloxane cross-linked copolymer in the copolymer composition varies according to the relative amounts of silane and protein/amino groups reacted together, as indicated above.

Accordingly, the present invention preferably comprises the copolymer of general formula (I):

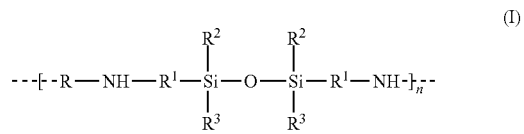

wherein

R is the residue of a hydrolysed protein R—NH$_2$; each R$^1$ is independently the residue of an organofunctional silane HR$^1$—Si(R$^{2'}$)(R$^{3'}$)—OH wherein R$^{2'}$ and R$^{3'}$ are each independently methyl, hydroxy, alkoxy having 1 to 6 carbon atoms;

R$^2$ and R$^3$ are each independently methyl, hydroxy, alkoxy having 1 to 6 carbon atoms or a residue of a compound of formula (IA):

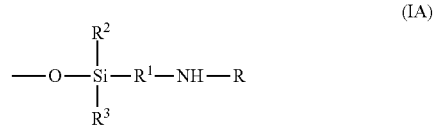

or (IB):

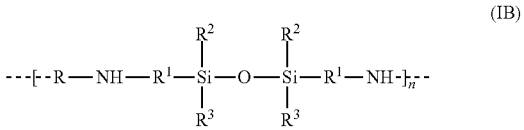

wherein R, R$^1$, R$^2$ and R$^3$ are each independently as defined; and n corresponds to the number of reacted amino groups, preferably in the range of from 1 to 101, having 0.1 to 0.4 silane molecule per reactive amino group of the protein.

R is preferably the residue of hydrolysed vegetable protein, such as hydrolysed wheat or potato protein, especially potato protein.

The nature of the group R$^1$, which is the residue of the organofunctional silane used for reaction with the protein component to form the copolymer, depends on the nature of the functional group originally present in the organofunctional silane. For example, when the functional group originally present in the organofunctional silane was an acyl halide, the group R$^1$ will typically contain a carbonyl group bonded directly to the nitrogen atom of the protein residue. Similarly, when the functional group originally present in the organofunctional silane was a sulphonyl halide, the group $R^1$ will typically contain a sulfonyl group bonded directly to the nitrogen atom of the protein residue. Preferably the group $R^1$ is derived from reaction of an organofunctional silane containing an epoxide groups as the functional group. In this case, in the final copolymer compound of formula (1), the group $R^1$ will contain a moiety of formula —$CH_2$—CH(OH)—, the methylene part of which is bonded directly to the nitrogen atom of the protein residue.

Preferably the group $R^1$ is an alkylene group having from 1 to 10 carbon atoms which may be interrupted by one or more oxygen atoms and may be substituted by one or more groups selected from hydroxy groups, halogen atoms, alkyl groups having from 1 to 6 carbon atoms and alkoxy groups having 1 to 6 carbon atoms.

More preferably, the group $R^1$ is a group of formula

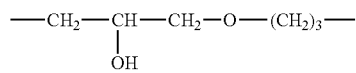

When the copolymer is not cross-linked, the groups $R^2$ and $R^3$ are each independently methyl, hydroxy, alkoxy having 1 to 6 carbon atoms. In the case of cross-linked copolymers, the polymer is cross-linked to a similar chain of formula (I) by condensation of two silanol groups to form a siloxane as in Reaction 1 above.

In the case of cross-linked copolymers, the compound of formula (IA) may comprise:

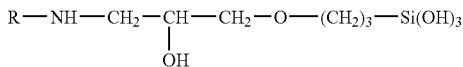

The copolymer preferably comprises a compound of formula (III)

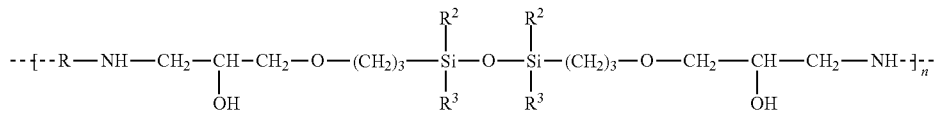

wherein R is a residue of hydrolysed wheat or potato protein; $R^2$ and $R^3$ are each other than methyl; and n is 1 to 4, preferably about 2.

Especially preferred is when the copolymer is hydrolysed vegetable protein 2-hydroxypropyl silanol.

In the copolymers for use in the invention, carboxyl groups of the protein component and/or amino groups of the protein component which are not bonded to the silicone component, can be chemically modified by reaction with a non-silicone, eg by esterification, acylation or quaternization.

Of the copolymers described above, particularly preferred for use in accordance with the present invention are copolymers formed by reacting a hydrolysed vegetable protein with a silane compound of formula (II):

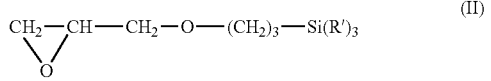

wherein each group R' is independently a hydroxy group or a group capable of hydrolysis to form a hydroxy group, the relative amounts of the hydrolysed protein and the silane being such that in the range of from 0.1 to 0.4 silane molecule is present for each reactive amino group of the protein, and, if necessary, one or both of the following steps (i) or (ii):
  (i) hydrolysis of any groups R' which are other than hydroxy groups to form a compound wherein R' is a hydroxy group, and
  (ii) cross-linking of the resulting copolymer.

According to a further preferred embodiment, the present invention comprises the copolymer of general formula (IV):

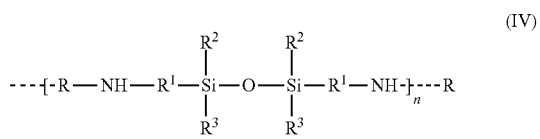

wherein

R is the residue of a hydrolysed protein R—$NH_2$ and $R^1$, $R^2$ and $R^3$ have the meanings as defined above.

The copolymers described above fall within the general disclosure of the applicant's European patent specification no EP 540 357. However, such copolymers are not specifically disclosed either in this document or any other prior art document. These copolymers are therefore new and form part of the present invention.

The present invention therefore provides in a further aspect a copolymer composition obtainable by reacting a hydrolysed vegetable protein with a silane compound of formula (II):

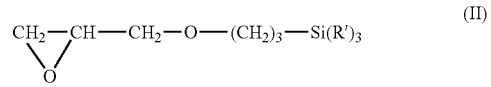

wherein each group R' is independently a methyl group, a hydroxy group or a group capable of hydrolysis to form a hydroxy group, provided that at least one of the R' groups represents a hydroxyl group or a group capable of hydrolysis to form a hydroxyl group, the relative amounts of the hydrolysed protein and the silane being such that in the range of from 0.1 to 0.4 silane molecule is present for each reactive amino group of the protein, and, if necessary, one or both of the following steps (i) or (ii):
  (i) hydrolysis of any groups R' which are other than hydroxy groups to form a compound wherein R' is a hydroxy group, and
  (ii) cross-linking of the resulting copolymer.

In the compounds of formula (II) used to prepare the novel copolymers of the present invention, each of the groups R' may independently be a hydroxy group (so that the compounds of formula (II) include a silanol group) or a group capable of hydrolysis to form a hydroxy group. Examples of suitable groups capable of hydrolysis to form a hydroxy group (ie functional groups attached to a silicon atom capable of hydrolyzing to produce a silanol) include halogen atoms and alkoxy groups having from 1 to 6 carbon atoms, preferably methoxy and ethoxy groups, and particularly preferably methoxy groups.

The copolymers of the present invention may be used to prepare simple aqueous compositions for application to the hair, such as an aqueous "leave on" composition or an aqueous "rinse off" composition.

For such compositions, a dilute solution of the copolymer in water may be used. The concentration of active ingredient in such a solution may range from 0.01% w/w to 10% w/w, and is preferably 0.05% w/w to 5% w/w, more preferably 0.5% w/w to 2% w/w, and most preferably about 1% w/w. Preferably, a buffered solution is used, in which the pH of the solution is adjusted to mildly acidic, with a pH in the range of from 5-6, using a base such as an alkali metal hydroxide, eg sodium hydroxide. In the case of rinse-off formulations, instructions are provided to wash off the copolymer solution after application; depending on the level of treatment required, such instructions may also require the solution to remain on the hair for some minutes, such as from 1 to 30 minutes. For leave-on formulations, the washing off step is omitted.

More preferred is when the composition is in the form of a shampoo, styling or conditioning composition, such as one for application to bleached, colored or normal (virgin, untreated) hair. Suitably, such compositions comprise from 0.05 to 20% w/w, preferably about 0.25 to 1% of the copolymer, based on the total weight of the composition.

Accordingly, the present invention further provides a composition, such as a shampoo, conditioner, styling composition or simple aqueous solution, comprising a protein-silane or -siloxane copolymer, as described above, in association with instructions for its use in preventing, treating or reducing damage to hair caused by flexure and/or abrasion thereof.

Such a composition and its associated instructions are conveniently provided in a package containing or including them. The package and/or composition may be provided with further components suitable for treating hair. In particular, the shampoo, styling or conditioner composition may comprise one or more of the standard ingredients thereof or carriers therefore, including but not limited to: include shine enhancers, moisturizers, herbal additives, hair strengtheners, vitamin additives, colorants, hair thickening agents; setting and styling agents; dandruff control agents; ultraviolet absorbers; essential oils and fragrances; anionic, non-ionic or cationic surfactants; thickening or viscosity-enhancing agents; detergents; stabilizing agents; emollients; chelating agents; sequestering agents; preservatives; disinfectants; anti-oxidants; antistatic agents; conditioning agents; detangling ingredients; emulsifying or dispersing agents; stimulants; soothers; solvents; carriers and the like.

The present invention will now be illustrated with reference to the following Examples, Test Exampler and Comparative Test Examples. However, it should be understood that the invention is not limited to or by these examples.

EXAMPLE 1

Preparation of Copolymer

The following steps were carried out:
1. Hydrosolanum (2000 g), a potato protein hydrolysate available from Croda Oleochemicals and having a weight average molecular weight ($M_w$) of 752, as measured by gel permeation chromatography [solvent: MeCN/$K_3PO_4$/NaCl (2:8); detector: UV at 220 nm; temperature: 40° C.; flow rate 0.600; standard: sodium polystyrene sulphonate; column TSK-GMPW] and mains water (760 g) were loaded into a suitable beaker and stirred. The solution was heated to 60° C.
2. The pH was adjusted to 10.2 using 25% sodium hydroxide (275.3 g).
3. Silquest A187 Silane (55.6 g), a compound of formula (A) below, (available from Cromptons SA, Kennet House, 4 Langley Quay, Slough, UK) was added over 120 minutes. The amount of Silquest A187 Silane added was calculated based on the Formol titer to give 20% substitution of the available amino groups.
4. During addition, pH was maintained in the range of 10-10.5 using 25% sodium hydroxide (25.2 g), and the temperature was kept constant at 60° C.
5. The reaction mixture was stirred for 4 hours at 60° C.
6. 28% hydrochloric acid (187.8 g) was added to lower the pH to 4.5.
7. Euxyl K300 (25.3 g), a preservative (supplied by Schülke & Mayr), was added and the solution stirred overnight at room temperature.
8. The pH was then checked and 28% hydrochloric acid (14.9 g) was added to bring it back to 4.5.
9. The liquor was then filtered through a depth filter pad to sparkling.

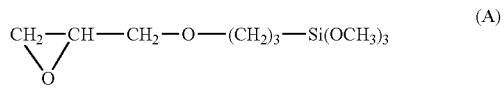

(A)

The resulting copolymer had a weight average molecular weight ($M_w$) of 2611, as measured using by gel permeation chromatography [solvent: MeCN/$K_3PO_4$/NaCl (2:8); detector: UV at 220 nm; temperature: 40° C.; flow rate 0.600; standard: sodium polystyrene sulphonate; column TSK-GMPW].

Flexabrasion Protocol

The Flexabrasion test is carried out using equipment specifically designed to assess the fatigue lifetime of a strand of hair through bending, straightening and abrasion. This piece of equipment has been built to mimic the interaction of hair against hair on the human head when it is being brushed. When a brush is pulled through the hair, the hair strands are entwined and move against one another, causing longitudinal shear within the fiber shaft, which will eventually cause longitudinal splitting and premature fracture.

As illustrated in FIG. 1, damage to the hair shaft is mimicked with this equipment as each strand of hair is being moved backwards and forwards over a piece of drawn rough Tungsten wire. This test method allows the evaluation of the effect of compositions on fatigue lifetime. It is a method that has already been used by Leroy F., Franbourg A., Grognet J. C., Vayssie C., Bauer D., as described in *Flexabrasion*. Poster at 1st Tricontinental Meet. Hair Res. Socs., Brussels, Oct. 8-10, (1995) and in the article 'Flexabrasion: A Method for Evaluating Hair Strength' by J. A. Swift, S. P. Chahal, D. L. Coulson and N. I. Challoner, Cosmetics and Toiletries, 2001, Vol 116, No 12, Pages 53-60, the entire contents of which are incorporated herein by reference thereto.

The flexabrasion equipment allows the testing of 20 hair segments at once. It is positioned in a humidity-controlled cabinet that allows the control of the relative humidity under which the hair is being tested.

TEST EXAMPLES

In the following Test Examples and Comparative Test Example, the following materials were used:
Virgin brown European hair (ex De Meo)
Bleached brown European hair (ex De Meo and bleached using the PVCS method detailed in Experiment I below)
Relaxed brown European hair (ex De Meo and relaxed using the method detailed in Experimental II below)
Permed brown European hair (ex De Meo and permed using the method detailed in Experiment III below)

Experiment 1—Bleaching Protocol—PVCS

| Materials | European brown hair (De Meo) |
|---|---|
| | Ammonium Persulphate |
| | 35% Hydrogen Peroxide |
| | Distilled Water |
| | pH Meter |
| | Gloves |
| | Goggles |

Procedure (carried out in a fume cupboard):
1. Weigh the hair to be bleached ($W_h$).
2. Calculate the amount of bleaching solution ($B_s$) using the weight ratio of 25/1 (Bleach solution/hair).
3. Calculate the amount of hydrogen peroxide ($H_p$) needed to make a 6% solution $H_p = B_s \times 0.06/0.3$.
4. Calculate amount of ammonium persulphate ($A_p$) needed for a 5% solution $A_p = 0.05 \times B_s$.
5. Pour about half the water needed into a beaker and bring the pH to 12 using sodium hydroxide.
6. Add the hydrogen peroxide and ammonium persulphate.
7. Adjust the pH to 9.5 using sodium hydroxide.
8. Add the rest of the water.
9. Immerse the hair into the bleaching solution for 30 minutes.
10. Rinse.
11. Allow dry overnight on a dry paper towel.

For each trial, brown European hair (ex De Meo) was used and mounted using the mounting procedure described in Experiment IV below.

Experiment II—Relaxing Protocol

| Materials Relaxer crème Base | % by Wt |
|---|---|
| Water | up to 100 |
| Polywax NF | 15.0 |
| Mineral Oil | 10.0 |
| Calcium Hydroxide | 5.0 |
| Volpo N10 | 2.0 |
| Propylene Glycol | 2.0 |
| Crodacol CS90 | 1.0 |

| Liquid Activator | % by Wt |
|---|---|
| Water | up to 100 |
| Guanidine Carbonate | 25.0 |
| Xanthan Gum | 0.2 |
| Preservative | qs |

| Neutralising Shampoo | % by Wt |
|---|---|
| Water | to 100 |
| Empicol ESB3/M | 20.0 |
| Incromine Oxide C | 3.0 |
| Incronom 30 | 6.0 |
| Lactic Acid | to pH 3.5–4 |
| Sodium Chloride | qs |

Procedure
1. Add liquid activator to the Relaxer creme and mix well.
2. Add segments and allow to soak for 15 minutes.
3. Rinse segments thoroughly under warm running water.
4. Soak segments in a 1:10 dilution of the neutralizing shampoo in water for 2 minutes.
5. Rinse segments thoroughly under warm water.
6. Treat immediately.

Experiment IIII—Perming Protocol
Materials
A Boots deep conditioning difficult to curl perming kit was used.
Perming Lotion
Water
Ammonium Thioglycolate
Ammonium Hydroxide
Ammonium Bicarbonate
PEG-40
Hydrogenated Castor Oil
Styrene/PVP copolymer
Imidazolidinyl Urea
Parfum
Sodium Gluceptate
Polyquaternium-6
Dimethicone
BHT—Butylated Hydroxytoluene
Neutralizer
Water
Hydrogen Peroxide
Sodium Laureth Sulphate
Polysorbate 20
TEA-cocoyl Hydrolysed Collagen
Phosphoric Acid
Disodium EDTA
Phenoxyethanol
Methylparaben
Ethylparaben
Sodium Stannate
Citric Acid Procedure
1. Allow segments to soak in the perming lotion for 25 minutes.
2. Rinse with warm running water.
3. Soak segments in the neutralizer for 10 minutes.
4. Rinse with warm running water.
5. Treat segments immediately.

For each trial, brown European hair (ex De Meo) was used and mounted using the procedure detailed in Experiment IV below.

Experiment IV—Standard Mounting Procedure
3 segments of 14 mm were cut from the root end of the hair (adjacent segments). Care was taken to avoid touching the hair segments. The segments were randomized and labeled A, B and C.

The following conditioner base was used in all of the studies:

Basic Hair Conditioner:

|  | % by Wt |
| --- | --- |
| Conditioner Base | 4 |
| Light Mineral Oil | 0.5 |
| Lactic Acid | to pH 4–4.5 |
| Water | to 100 |
| Perfume, Preservative, Colour | |

TEST EXAMPLE 1

Effect of Copolymer of Example 1 in a conditioner base (1% w/w as supplied) on the flexabrasion lifetime of bleached hair.

Segments B and C were bleached using the protocol detailed in Experiment I and then dried overnight at ambient temperature and relative humidity. The A segments were soaked in water at pH 5.5 for 30 minutes and then dried overnight at ambient temperature and relative humidity. These segments were then glued onto the flattened crimps and mounted as described in Experiment IV above.

The A segments were then soaked in water (pH 5.5) at 35° C. for 6 minutes and again dried overnight at ambient temperature and humidity. The B segments were soaked in the conditioner base at 35° C. for 2 minutes, then rinsed in water at 35° C. This was repeated twice further. The C segments were soaked in the test conditioner (conditioner plus copolymer, 1% w/w as supplied) at 35° C. for 2 minutes, then rinsed in water at 35° C. This was repeated twice further.

All segments were allowed to dry overnight at ambient temperature and humidity. The segments were then placed on the flexabrasion apparatus illustrated in FIG. 1 and allowed to equilibrate at 60% relative humidity for 1 hour. During this time, the segments were not under load. The segments were then lowered and the flexabrasion equipment run. The fatigue lifetime of each segments was recorded and the data analyzed statistically.

A percentage calculation has been used to report the results in a format expressing the effect of the treatment on the segments compared to the control. The calculation is as follows:

Percentage Difference=$((B-A)/A) \times 100$

Where:
A=Control segments fatigue lifetime
B=Test segments fatigue lifetime

This was calculated for each set of segments before being averaged. This calculation gives a percentage increase or decrease.

Figure 2:
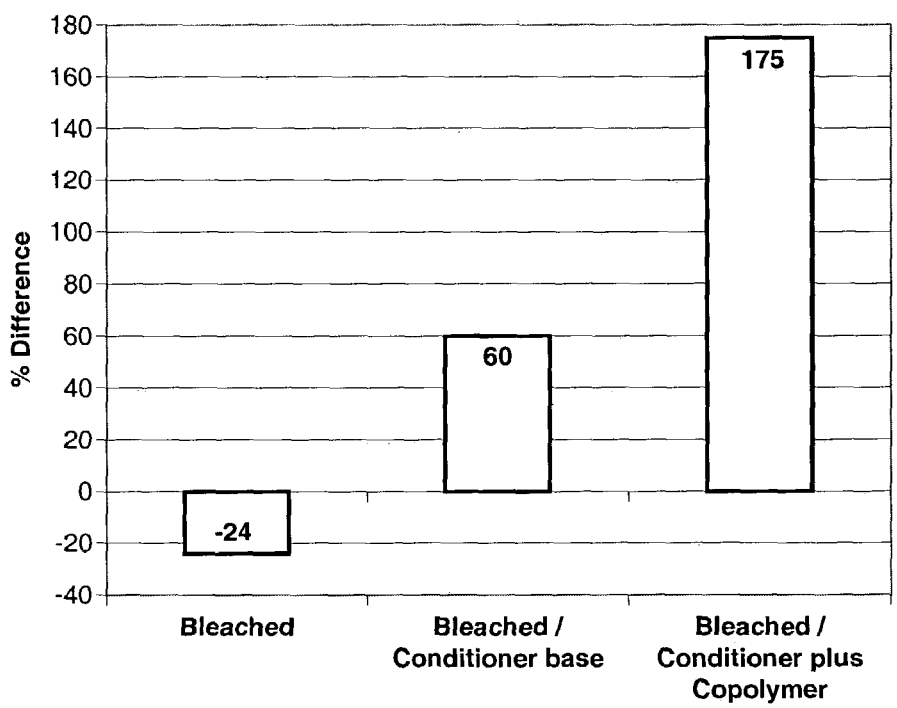
FIG. 2 is a graphic representation of test results on bleached hair, bleached hair treated with conditioner base and bleached hair treated with conditioner plus a copolymer according to Test Example 1.

These results are shown in Table 1 and FIG. 2.

This study indicates that by bleaching hair segments and subsequently treating them with the conditioner base (control), there is an improvement in fatigue lifetime of 60%; this was analyzed statistically using the Student's t-test and found to be a significant difference ($p=0.017$).

However, there was observed an increase of 175% in fatigue lifetime when the bleached segments were treated with the conditioner containing the copolymer, in comparison to the virgin control segments. Again, this difference was analyzed statistically using the Student's t-test and found to be statistically significant ($p=0.016$).

The above results show that, when comparing the effect of the conditioner containing the copolymer on bleached hair with that of the conditioner base when used alone, there is a statistically significant improvement of 130% ($p=0.047$) in fatigue lifetime.

TEST EXAMPLE 2

Effect of Copolymer of Description 1 in a conditioner base (0.25% w/w active) on the flexabrasion lifetime of relaxed hair—one treatment for 2 minutes.

Segments A, B and C were glued onto the flattened crimps and mounted as described in Experiment IV above.

Segments B and C were relaxed using the protocol detailed in experiment 11 above.

The A segments were soaked in water at pH 5.5 for 17 minutes.

The A segments were soaked in water for 2 minutes and then dried overnight at ambient temperature and humidity.

The B segments were soaked in the conditioner base and water (1:5 ratio) at 40° C. for 2 minutes, then rinsed in water a 40° C.

The C segments were soaked in the test conditioner (conditioner plus copolymer, 0.25% w/w active) and water (1:5 ratio) at 40° C. for 2 minutes, then rinsed in water at 40° C.

All segments were allowed to dry overnight at ambient temperature and humidity. The segments were then placed on the flexabrasion apparatus illustrated in FIG. 1 and allowed to equilibrate at 60% relative humidity for 1 hour. During this time, the segments were not under load. The segments were then lowered and the flexabrasion equipment run. The fatigue lifetime of each segments was recorded and the data analyzed statistically.

Figure 3:
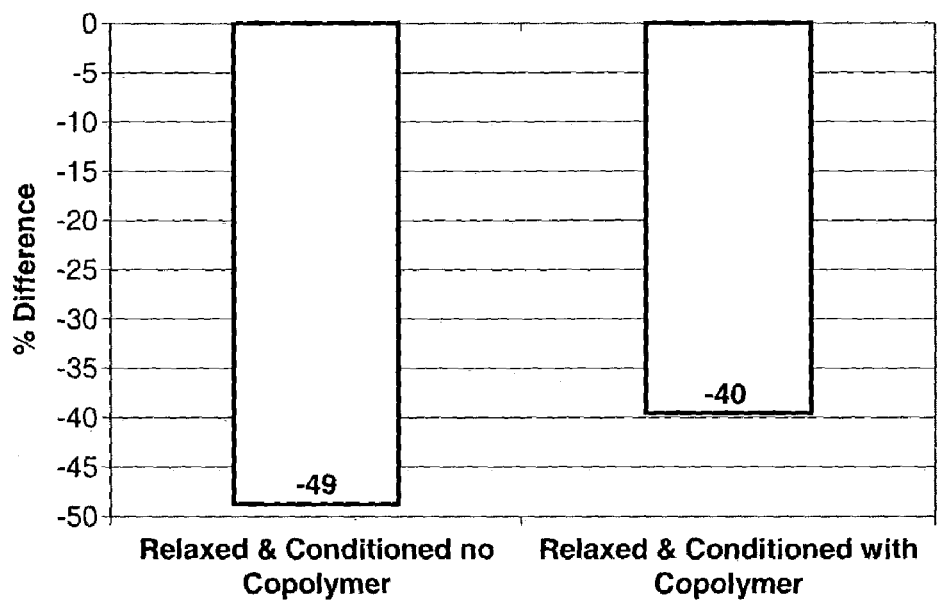
FIG. 3 is a graphic representation of test results of flexabrasion lifetime of relaxed hair according to Test Example 2.

The results are shown in Table 2 and FIG. 3, and are reported using the same percentage calculation method used to report the results of Test Example 1.

TABLE 1

| | Segments | | | % Difference | | |
| --- | --- | --- | --- | --- | --- | --- |
| Hair | A | B | C | B to A | C to A | C to B |
| Population | 32 | 32 | 32 | 32 | 32 | 32 |
| Mean | 1008 | 1237 | 1598 | 60 | 175 | 130 |
| S.D | 764 | 994 | 1497 | 134 | 389 | 355 |
| Variance | 583588 | 988730 | 2239982 | 17984 | 151485 | 126179 |
| P | | | | 0.017 | 0.016 | 0.047 |

TABLE 2

| | Virgin | Relaxed & Conditioned no Copolymer Segments | Relaxed & Conditioned with Copolymer | % Difference | | |
|---|---|---|---|---|---|---|
| | A | B | C | B to A | C to A | C to B |
| Population | 24 | 24 | 24 | 24 | 24 | 24 |
| Mean | 425 | 220 | 268 | −49 | −40 | 45 |
| S.D | 425 | 284 | 410 | 28 | 53 | 104 |
| Variance | 180249 | 80784 | 167695 | 762 | 2793 | 10867 |
| p | | | | <0.005 | <0.005 | NS |

NS = Not significant

This study indicates that by relaxing hair segments and subsequently treating them with the conditioner base (control), there is a reduction in fatigue lifetime of 49%; this was analyzed statistically using the Student's t-test and found to be a significant difference ($p<0.005$).

However, there was observed a decrease of 40% in fatigue lifetime when the relaxed segments were treated with the conditioner containing the copolymer, in comparison with the virgin control segments. Again, this difference was analyzed statistically using the Student's t-test and found to be statistically significant ($p<0.005$).

This indicates that addition of the copolymer of the present invention to the conditioner improved the conditioning benefits by 9%.

TEST EXAMPLE 3

Effect of Copolymer of Example 1 in a conditioner base (0.25% w/w active) on the flexabrasion lifetime of relaxed hair—one treatment for 6 minutes.

Segments A, B and C were glued onto the flattened crimps and mounted as described in Experiment IV above.

Segments B and C were relaxed using the protocol detailed in Experiment II.

The A segments were soaked in water at pH 5.5 for 17 minutes.

The A segments were soaked in water for 6 minutes and then dried overnight at ambient temperature and humidity.

The B segments were soaked in the conditioner base and water (1:2 ratio) at 40° C. for 6 minutes, then rinsed in water at 40° C.

The C segments were soaked in the test conditioner (conditioner plus copolymer, 0.25% w/w active) and water (1:2 ratio) at 40° C. for 6 minutes, then rinsed in water at 40° C.

All segments were allowed to dry overnight at ambient temperature and humidity. The segments were then placed on the flexabrasion apparatus and allowed to equilibrate at 60% relative humidity for 1 hour. During this time, the segments were not under load. The segments were then lowered and the flexabrasion equipment run. The fatigue lifetime of each segments was recorded and the data analyzed statistically.

Figure 4:
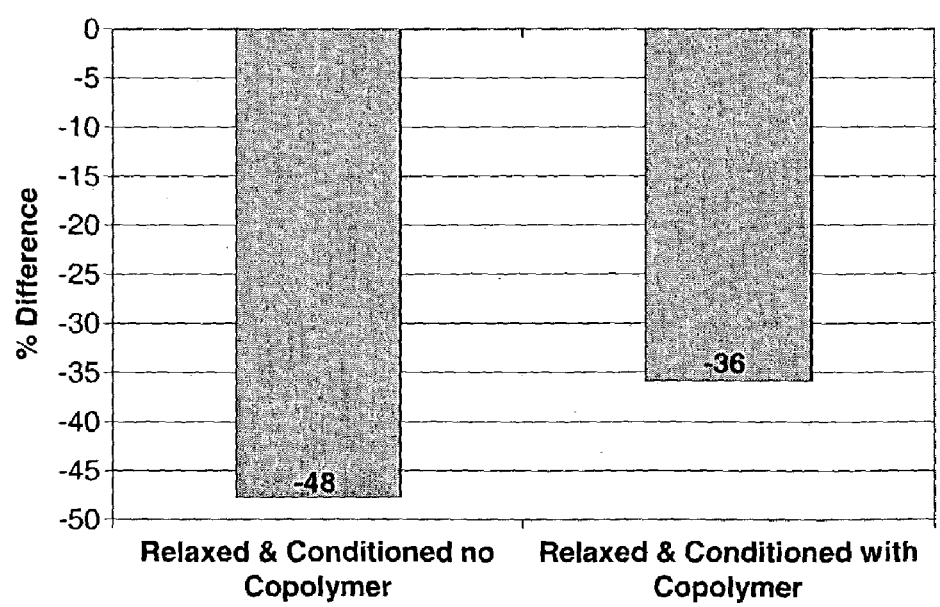
FIG. 4 is a graphic representation of test results of flexabrasion lifetime of relaxed hair according to Test Example 3.

The results are shown in Table 3 below and FIG. 4. The results are reported using the same percentage calculation procedure used to report the results of Test Example 1.

TABLE 3

| | Virgin | Relaxed & Conditioned no Copolymer Segments | Relaxed & Conditioned with Copolymer | % Difference | | |
|---|---|---|---|---|---|---|
| | A | B | C | B to A | C to A | C to B |
| Population | 28 | 28 | 28 | 28 | 28 | 28 |
| Mean | 401 | 207 | 270 | −48 | −36 | 80 |
| S.D | 406 | 274 | 380 | 36 | 48 | 158 |
| Variance | 164972 | 75082 | 144256 | 1262 | 2346 | 25084 |
| p | | | | <0.005 | <0.005 | NS |

This study indicates that by relaxing hair segments and subsequently treating them with the conditioner base (control), there is a reduction in fatigue lifetime of 48%; this was analyzed statistically using the Student's t-test and found to be a significant difference ($p<0.005$).

However, there was observed a decrease of only 36% in fatigue lifetime when the relaxed segments were treated with the conditioner containing the copolymer according to the present invention, in comparison with the virgin control segments. Again, this difference was analyzed statistically using the Student's t-test and found to be statistically significant ($p<0.005$).

This indicates that addition of the copolymer of the present invention to the conditioner improves the conditioning benefits by 12%.

TEST EXAMPLE 4

Effect of Copolymer of Example 1 in a conditioner base (0.25% w/w active) on the flexabrasion lifetime of permed hair—three treatments for 2 minutes.

Segments A, B and C were glued onto the flattened crimps and mounted as described in Experiment IV above.

Segments B and C were permed using the protocol detailed in Experiment III.

The A segments were soaked in water at pH 5.5 for 35 minutes.

The A segments were soaked in water for 6 minutes and then dried overnight at ambient temperature and humidity. The B segments were soaked in the conditioner base and water (1:2 ratio) at 40° C. for 2 minutes. This was then repeated a further 2 times and then the segments were rinsed in water at 40° C. The C segments were soaked in the test conditioner (conditioner plus copolymer, 0.25% w/w active) and water (1:2 ratio) at 40° C. for 2 minutes. This was then repeated a further 2 times. The segments were then rinsed in water at 40° C.

All segments were allowed to dry overnight at ambient temperature and humidity. The segments were then placed on the flexabrasion apparatus and allowed to equilibrate at 60% relative humidity for 1 hour. During this time, the segments were not under load. The segments were then lowered and the flexabrasion equipment run. The fatigue lifetime of each segments was recorded and the data analyzed statistically.

Figure 5:
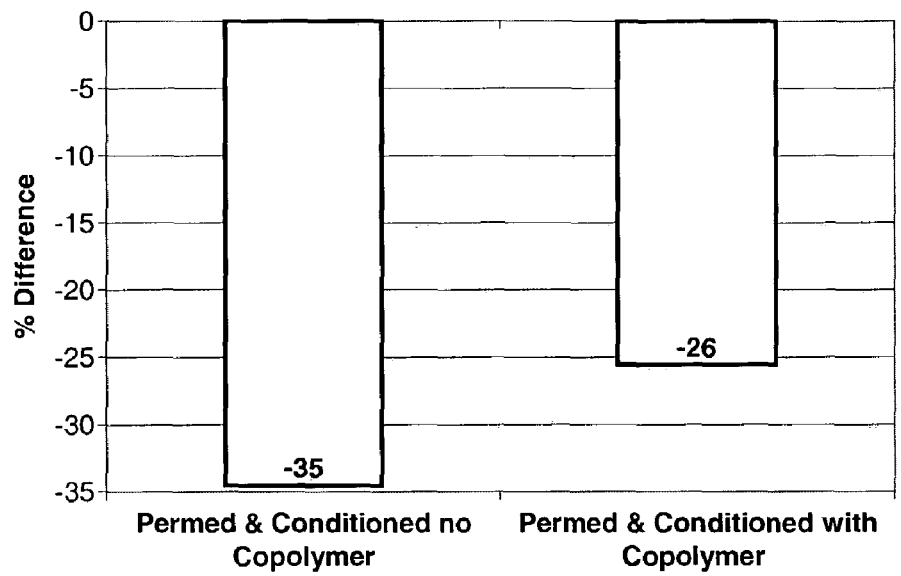
FIG. 5 is a graphic representation of test results of flexabrasion lifetime of permed hair according to Test Example 4.

The results are shown in Table 4 below and FIG. 5, using the same percentage calculation method used to report the results of Test Example 1.

TABLE 4

|  | Virgin | Permed & Conditioned no Copolymer Segments | Permed & Conditioned with Copolymer | % Difference | | |
|---|---|---|---|---|---|---|
|  | A | B | C | B to A | C to A | C to B |
| Population | 18 | 18 | 18 | 18 | 18 | 18 |
| Mean | 694 | 423 | 514 | −35 | −26 | 160 |
| S.D | 608 | 544 | 613 | 48 | 57 | 473 |
| Variance | 369705 | 296261 | 375348 | 2302 | 3282 | 223898 |
| p |  |  |  | 0.076 | 0.007 | NS |

This study indicates that by perming hair segments and subsequently treating them with the conditioner base (control), results in a reduction in fatigue lifetime of 40%; this was analyzed statistically using the Student's t-test and found to be a significant difference (p=0.007).

However, there was observed a decrease only 26% in fatigue lifetime when the permed segments were treated with the conditioner containing the copolymer of the present invention, in comparison with the virgin control segments. Again, this difference was analyzed statistically using the Student's t-test and found to be statistically significant (p=0.076).

This indicates that addition of the copolymer of the present invention to the conditioner improves the conditioning benefits seen by 9%.

TEST EXAMPLE 5

Effect of Copolymer of Example 1 in a conditioner base (0.25% w/w active) on the flexabrasion lifetime of permed hair—one treatment for 6 minutes.

Segments A, B and C were glued onto the flattened crimps and mounted as described in Experiment IV above.

Segments B and C were permed using the protocol detailed in Experiment III above.

The A segments were soaked in water at pH 5.5 for 35 minutes.

The A segments were soaked in water for 6 minutes and then dried overnight at ambient temperature and humidity.

The B segments were soaked in the conditioner base and water (1:2 ratio) at 40° C. for 6 minutes, then the segments were rinsed in water at 40° C.

The C segments were soaked in the test conditioner (conditioner plus copolymer, 0.25% w/w active) and water (1:2 ratio) at 40° C. for 6 minutes, the segments were then rinsed in water at 40° C.

All segments were allowed to dry overnight at ambient temperature and humidity. The segments were then placed on the flexabrasion apparatus and allowed to equilibrate at 60% relative humidity for 1 hour. During this time, the segments were not under load. The segments were then lowered and the flexabrasion equipment run. The fatigue lifetime of each segments was recorded and the data analyzed statistically.

Figure 6:
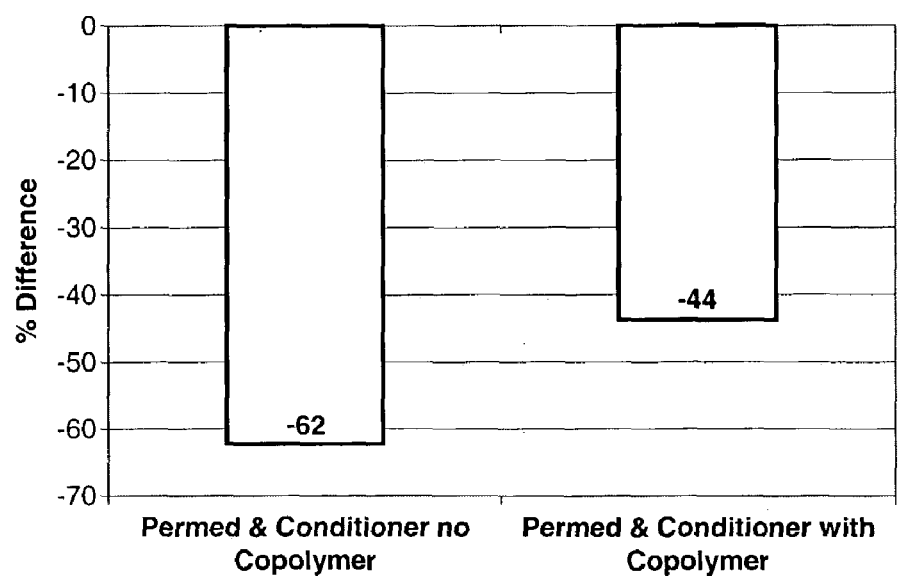
FIG. 6 is a graphic representation of test results of flexabrasion lifetime of permed hair according to Test Example 5.

The results are shown in Table 5 below and in FIG. 6, using the same percentage calculation method used to report the results of Test Example I.

TABLE 5

|  | Virgin | Permed & Conditioner no Copolymer Segments | Permed & Conditioner with Copolymer | % Difference | | |
|---|---|---|---|---|---|---|
|  | A | B | C | B to A | C to A | C to B |
| Population | 18 | 18 | 18 | 18 | 18 | 18 |
| Mean | 530 | 217 | 290 | −62 | −44 | 70 |
| S.D | 532 | 285 | 350 | 27 | 58 | 167 |
| Variance | 282844 | 81117 | 122261 | 730 | 3367 | 27760 |
| p |  |  |  | 0.006 | <0.005 | NS |

This study indicates that by perming hair segments and subsequently treating them with the conditioner base (control) results in a reduction in fatigue lifetime of 62%; this was analyzed statistically using the Student's t-test and found to be a significant difference (p<0.005).

However, a decrease of 44% in fatigue lifetime was observed when the permed segments were treated with the conditioner containing the copolymer of the present invention, in comparison with the virgin control segments. Again, this difference was analyzed statistically using the Student's t-test and found to be statistically significant (p=0.006).

This indicates that addition of the copolymer of the present invention to the conditioner improves the conditioning benefits seen by 18%.

TEST EXAMPLE 6

Effect of Copolymer of Example 1 in an aqueous solution (1% w/w active) on the flexabrasion lifetime of bleached hair.

Segments B and C were bleached using the protocol detailed in Experiment I and then dried overnight at ambient temperature and relative humidity. The A segments were soaked in water at pH 5.5 for 30 minutes and then dried overnight at ambient temperature and relative humidity. These segments were then glued onto the flattened crimps and mounted as described in Experiment IV above.

The A and B segments were then soaked in water (pH 5.5) for 10 minutes and again dried overnight at ambient temperature and humidity. The C segments were soaked in the aqueous solution of copolymer of description 1 (1% w/w actives) for 10 minutes.

All segments were allowed to dry overnight at ambient temperature and humidity. The segments were then placed on the flexabrasion apparatus and allowed to equilibrate at 60% relative humidity for 1 hour. During this time, the segments were not under load. The segments were then lowered and the flexabrasion equipment run. The fatigue lifetime of each segment was recorded and the data analyzed statistically.

The results are shown in Table 6 below and in FIG. 7, using the same percentage calculation method used to report the results of Test Example 1.

TABLE 6

| Hair | Virgin | Bleached Segments | Bleached/ copolymer | % Difference | | |
|---|---|---|---|---|---|---|
| | A | B | C | B to A | C to A | C to B |
| Population | 16 | 16 | 16 | 16 | 16 | 16 |
| Mean | 1237 | 749 | 1129 | −20 | 0 | 38 |
| S.D | 1079 | 481 | 934 | 38 | 45 | 61 |
| Variance | 1164457 | 231060 | 872040 | 1422 | 2006 | 3709 |
| P | | | | <0.05 | <0.1 | <0.05 |

This study indicates that after treating bleached hair with a 1% w/w active aqueous solution of the copolymer of the present invention no difference in flexabrasion lifetime can be observed compared to virgin unbleached hair. Also the study indicated that by treating the bleached hair with the solution of the copolymer composition of the present invention an improvement of 38% (P<0.05) was observed in flexabrasion lifetime compared to the bleached only hair segments.

COMPARATIVE TEST EXAMPLE

Effect of Crodasone W (the Product of Example 2 of EP 540357) in an Aqueous Solution (1% w/w Active) on the Flexabrasion Lifetime of Bleached Hair Segments B and C were bleached using the protocol detailed in Experiment I above and then dried overnight at ambient temperature and relative humidity. The A segments were soaked in water at pH 5.5 for 30 minutes and then dried overnight at ambient temperature and relative humidity. These segments were then glued onto the flattened crimps and mounted as described in Experiment IV above.

The A and B segments were then soaked in water (pH 5.5) for 10 minutes and again dried overnight at ambient temperature and humidity. The C segments were soaked in a 1% w/w actives aqueous solution of Crodasone W (the copolymer of Example 2 of EP 540357) for 10 minutes.

All segments were allowed to dry overnight at ambient temperature and humidity. The segments were then placed on the flexabrasion and allowed to equilibrate at 60% relatively humidity for 1 hour. During this time, the segments were not under load. The segments were then lowered and the flexabrasion equipment run. The fatigue lifetime of each segments was recorded and the data analyzed statistically.

The results are shown in Table 7 below and FIG. 8, using the same percentage calculation method used to report the results of Test Example I.

TABLE 7

| | Virgin | Bleached Segments | Bleached/ Crodasone W | % Differences | | |
|---|---|---|---|---|---|---|
| | A | B | C | B to A | C to A | C to B |
| Population | 16 | 16 | 16 | 16 | 16 | 16 |
| Mean | 1381 | 887 | 807 | −34 | −30 | −97 |
| S.D | 1029 | 862 | 752 | 37 | 56 | 215 |
| Variance | 1059617 | 742746 | 565031 | 1332 | 3104 | 46189 |
| P | | | | <0.005 | <0.05 | NS |

This study indicated that treatment of bleached hair with a 1% active aqueous solution of Crodasone W for 10 minutes did not improve the flexabrasion lifetime of the hair.

Significantly, a comparison of the results of Test Example 6 and the comparative Test Example indicates that treatment of hair with the copolymer composition of the present invention confers a marked and significant improvement in flexabration lifetime when compared with hair treated with the commercially available copolymer Crodasone W.

The invention claimed is:

1. A protein-silane and/or protein-siloxane copolymer obtainable by reacting a protein having at least one reactive amino group and a silane compound, the relative amounts of the protein and the silane compound being such that in the range of from 0.1 to 0.4 moles of silane are present per mole of reactive amino group of the protein, and that the copolymer having the general formula (I):

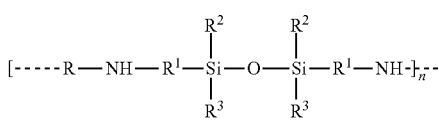

wherein

R is the residue of a hydrolysed protein R—$NH_2$; each $R^1$ and $R^{1'}$ is independently the residue of the silane compound wherein the silane compound is an organofunctional silane;

$R^2$ and $R^3$ are each independently methyl, hydroxy, alkoxy having 1 to 6 carbon atoms or a residue of a compound of formula (IA):

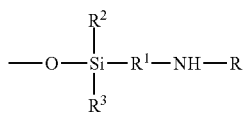

or (IB):

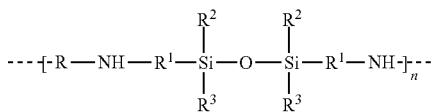

wherein R, $R^1$, $R^{1'}$, $R^2$ and $R^3$ are each independently as defined; and n corresponds to the number of reacted amino groups, and the copolymer has a weight average molecular weight of from 295 D to 3 kD.

2. The copolymer of claim 1, wherein R is the residue of hydrolysed vegetable protein.

3. The copolymer of claim 2, wherein R is the residue of hydrolysed potato protein.

4. The copolymer of claim 1, wherein $R^1$ is

—$CH_2$—CH—$CH_2$—O—$(CH_2)_3$—.
|
OH

5. The copolymer of claim 1, wherein the weight average molecular weight of the protein component is from 350-1000 Daltons.

6. The copolymer of claim 1, wherein the weight average molecular weight of the protein component is in the range of 600-800 Daltons.

7. The copolymer of claim 1, having a weight average molecular weight in the range of 1.5 to 3 kD.

8. The copolymer of claim 1, wherein $R^1$ contains a moiety —$CH_2$—CH(OH)—.

9. The copolymer of claim 8, wherein the methylene part of the moiety is bonded directly to a nitrogen atom of the protein residue.

10. The copolymer of claim 1, wherein the compound of formula (I) comprises:

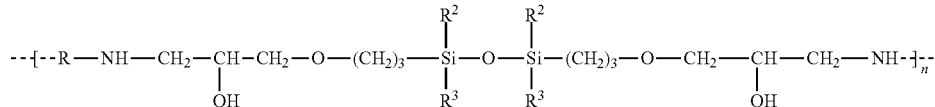

wherein R is a residue of hydrolysed wheat or potato protein; $R^2$ and $R^3$ are as previously defined with the proviso that neither is methyl; and n is in the range of from 1 to 4.

11. The copolymer of claim 10, wherein n is about 2.

12. The copolymer of claim 1, wherein n is in the range from 1 to 101.

13. The copolymer of claim 1 wherein $R^{1'}$ is

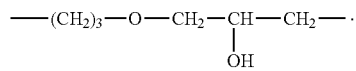

14. The copolymer of claim 1, wherein $R^{1'}$ contains a moiety —$CH_2$—CH(OH)—.

15. The copolymer of claim 1, wherein the weight average molecular weight of the copolymer is 295D-1000D.

16. The copolymer of claim 1, wherein the weight average molecular weight of the copolymer is 295-1.5kD.

* * * * *

UNITED STATES PATENT AND TRADEMARK OFFICE
CERTIFICATE OF CORRECTION

PATENT NO. : 8,048,846 B2
APPLICATION NO. : 10/388180
DATED : November 1, 2011
INVENTOR(S) : Surinder Pall Chahal, Alun Robert Barnes and Nicholas Ian Challoner It is certified that error appears in the above-identified patent and that said Letters Patent is hereby corrected as shown below:

In the Claims

Claim 1, Column 21, beginning at Line 5, should read:

(I)

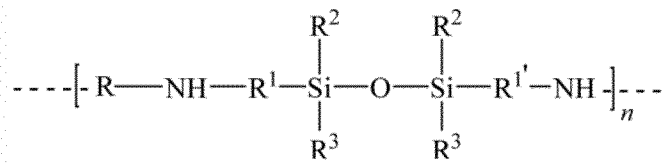

Claim 1, Column 21, beginning at Line 28, should read:

(IB)

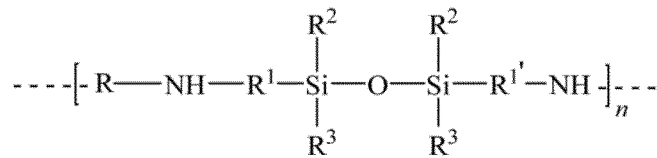

Signed and Sealed this
Nineteenth Day of April, 2022

Katherine Kelly Vidal
*Director of the United States Patent and Trademark Office*